United States Patent
Lam et al.

(10) Patent No.: US 7,211,196 B2
(45) Date of Patent: May 1, 2007

(54) METHOD AND SYSTEM OF DISCRIMINATING SUBSTRATE TYPE

(75) Inventors: Hieu A. Lam, Richardson, TX (US); Hongyu Yue, Austin, TX (US)

(73) Assignee: Tokyo Electron Limited, Tokyo (JP)

( * ) Notice: Subject to any disclaimer, the term of this patent is extended or adjusted under 35 U.S.C. 154(b) by 0 days.

(21) Appl. No.: 10/809,474

(22) Filed: Mar. 26, 2004

(65) Prior Publication Data
US 2005/0211669 A1    Sep. 29, 2005

(51) Int. Cl.
*H01L 21/66* (2006.01)
(52) U.S. Cl. .............. 216/59; 438/9; 438/16
(58) Field of Classification Search .......... None
See application file for complete search history.

(56) References Cited

U.S. PATENT DOCUMENTS

| | | | | |
|---|---|---|---|---|
| 5,788,869 A | * | 8/1998 | Dalton et al. | 216/60 |
| 5,877,032 A | * | 3/1999 | Guinn et al. | 438/9 |
| 6,046,796 A | * | 4/2000 | Markle et al. | 356/72 |
| 6,060,328 A | * | 5/2000 | En et al. | 438/9 |
| 6,950,178 B2 | * | 9/2005 | Rueger et al. | 356/72 |
| 2003/0052083 A1 | * | 3/2003 | Kim et al. | 216/59 |

* cited by examiner

*Primary Examiner*—Anita Alanko
(74) *Attorney, Agent, or Firm*—Oblon, Spivak, McClelland, Maier & Neustadt, P.C.

(57) ABSTRACT

A method and system for determining a substrate type during a seasoning process is presented. An optical signal is acquired from a process in a plasma processing system, and the optical signal is compared to a pre-determined threshold value. Depending upon the comparison, the substrate type is determined to be of a correct type, or an incorrect type.

8 Claims, 9 Drawing Sheets

METHOD AND SYSTEM OF DISCRIMINATING SUBSTRATE TYPE

FIELD OF THE INVENTION

The present invention relates to a method and system for discriminating substrate type and, in particular, to a method and system for discriminating a substrate type during a seasoning process.

BACKGROUND OF THE INVENTION

The fabrication of integrated circuits (IC) in the semiconductor industry typically employs plasma to create and assist surface chemistry within a plasma reactor necessary to remove material from and deposit material to a substrate. In general, plasma is formed within the plasma reactor under vacuum conditions by heating electrons to energies sufficient to sustain ionizing collisions with a supplied process gas. Moreover, the heated electrons can have energy sufficient to sustain dissociative collisions, and therefore, a specific set of gases under predetermined conditions (e.g., chamber pressure, gas flow rate, etc.) are chosen to produce a population of charged species and chemically reactive species suitable to the particular process being performed within the chamber (e.g., etching processes where materials are removed from the substrate or deposition processes where materials are added to the substrate).

Typically, during plasma processing such as for example during etch applications, it is necessary to "season" the plasma processing system following a period of process system maintenance, i.e. chamber cleaning, process kit replacement, etc. Prior to initiating production, several substrates are processed through the plasma processing system in order to form a "seasoning" film on the chamber interior and, thus, facilitate repeatable process performance for the substrates to follow. The substrates used for "seasoning" are generally coated with a seasoning material, such as photoresist, to provide a proper seasoning film on the chamber interior. However, during a seasoning process, a non-seasoning substrate, such as a bare silicon substrate, can be mistakenly inserted into the seasoning process. When this occurs, significant particle production and contamination in the seasoned chamber can lead to poor quality production substrates and chamber downtime.

SUMMARY OF THE INVENTION

One aspect of the present invention is to reduce or eliminate any or all of the above-described problems.

Another object of the present invention is to provide a method and system for distinguishing substrate type. According to one aspect of the invention, a method for determining a substrate type is presented comprising: disposing the substrate in a plasma processing system; exposing the substrate to a process in the plasma processing system; detecting an optical signal from the process; and determining the substrate type by comparing the optical signal with a threshold value.

According to another aspect of the invention, a system for determining a substrate type comprising: a diagnostic system configured to be coupled with a plasma processing system, and configured to provide an optical signal from a process in the plasma processing system; and a controller coupled to the diagnostic system and configured to determine the substrate type by comparing the optical signal to a threshold value. According to yet another aspect of the invention, a method for determining a substrate type is presented comprising: disposing the substrate in a plasma processing system; exposing the substrate to a seasoning process in the plasma processing system; detecting an optical signal from the process using optical emission spectroscopy, wherein the optical signal comprises an intensity ratio of a first intensity corresponding to a first wavelength band to a second intensity corresponding to a second wavelength band; and determining the substrate type by comparing the optical signal with a threshold value, wherein the threshold value is set to an average value between an intensity ratio for a correct substrate type and an intensity ratio for an incorrect substrate type.

DETAILED DESCRIPTION OF SEVERAL EMBODIMENTS

Figure 1:
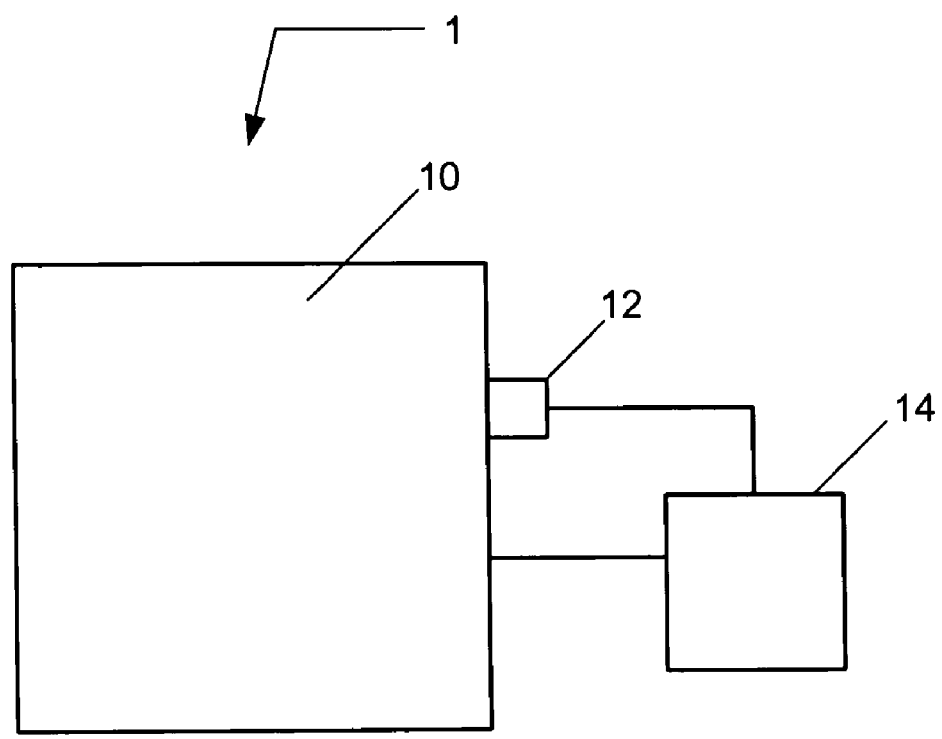
FIG. 1 shows a simplified schematic diagram of a plasma processing system according to an embodiment of the invention.

According to one embodiment, a plasma processing system 1 is depicted in FIG. 1 comprising a plasma processing chamber 10, a diagnostic system 12 coupled to the plasma processing chamber 10, and a controller 14 coupled to the diagnostic system 12 and the plasma processing chamber 10. The controller 14 is configured to execute a process recipe comprising at least one of an etch recipe, and a seasoning recipe. Additionally, controller 14 is configured to receive at least one optical signal from the diagnostic system 12 and to post-process the at least one optical signal in order to accurately determine a substrate type for the substrate present in the plasma processing chamber 10. In the illustrated embodiment, plasma processing system 1, depicted in FIG. 1, utilizes a plasma for material processing. Plasma processing system 1 can comprise an etch chamber, and ash chamber, or combination thereof.

Figure 2:
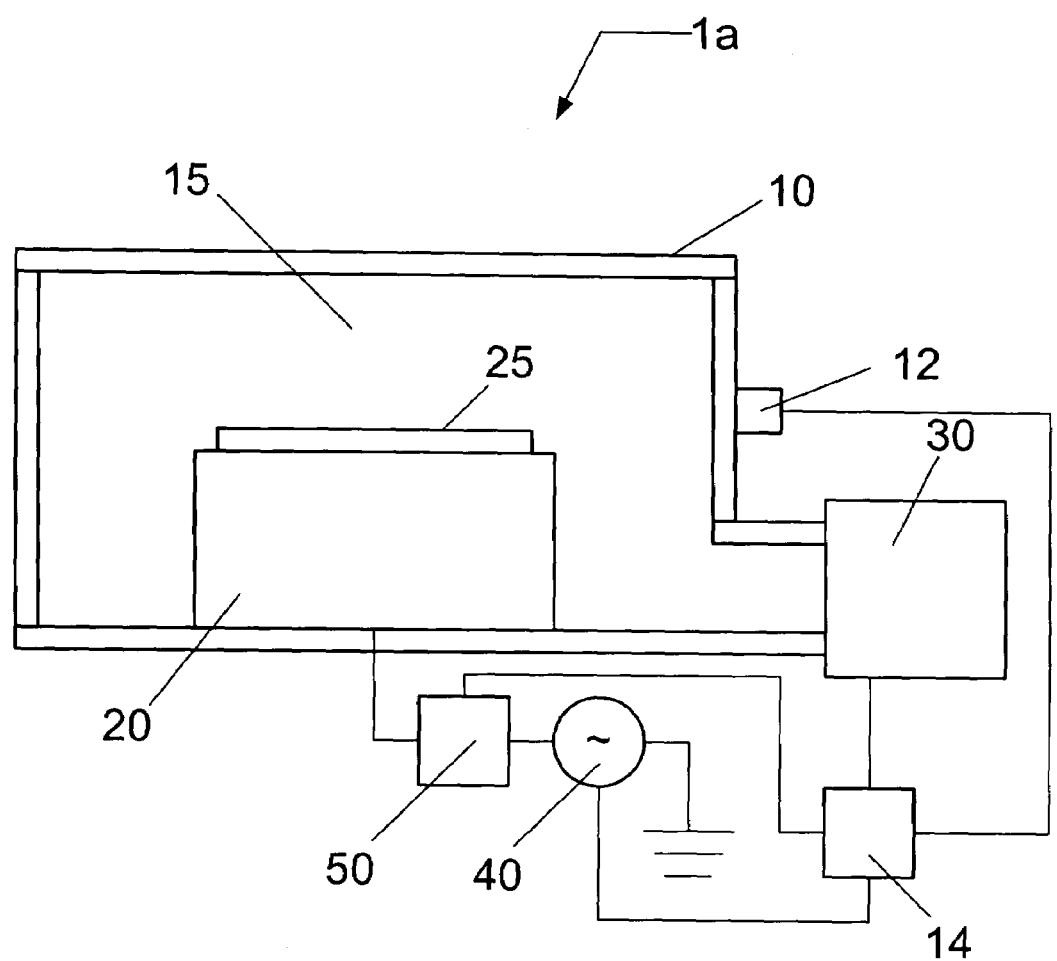
FIG. 2 shows a schematic diagram of a plasma processing system according to another embodiment of the invention.

According to the embodiment depicted in FIG. 2, plasma processing system 1a can comprise plasma processing chamber 10, substrate holder 20, upon which a substrate 25 to be processed is affixed, and vacuum pumping system 30. Substrate 25 can be, for example, a semiconductor substrate, a wafer or a liquid crystal display. Plasma processing chamber 10 can be, for example, configured to facilitate the generation of plasma in processing region 15 adjacent a surface of substrate 25. An ionizable gas or mixture of gases is introduced via a gas injection system (not shown) and the process pressure is adjusted. For example, a control mechanism (not shown) can be used to throttle the vacuum pumping system 30. Plasma can be utilized to create materials specific to a pre-determined materials process, and/or to aid the removal of material from the exposed surfaces of substrate 25. The plasma processing system 1a can be configured to process 200 mm substrates, 300 mm substrates, or larger.

Substrate 25 can be, for example, affixed to the substrate holder 20 via an electrostatic clamping system. Furthermore, substrate holder 20 can, for example, further include a cooling system including a re-circulating coolant flow that receives heat from substrate holder 20 and transfers heat to a heat exchanger system (not shown), or when heating, transfers heat from the heat exchanger system. Moreover, gas can, for example, be delivered to the back-side of substrate 25 via a backside gas system to improve the gas-gap thermal conductance between substrate 25 and substrate holder 20. Such a system can be utilized when temperature control of the substrate is required at elevated or reduced temperatures. For example, the backside gas system can comprise a two-zone gas distribution system, wherein the helium gas gap pressure can be independently varied between the center and the edge of substrate 25. In other embodiments, heating/cooling elements, such as resistive heating elements, or thermoelectric heaters/coolers can be included in the substrate holder 20, as well as the chamber wall of the plasma processing chamber 10 and any other component within the plasma processing system 1a.

In the embodiment shown in FIG. 2, substrate holder 20 can comprise an electrode through which RF power is coupled to the processing plasma in process space 15. For example, substrate holder 20 can be electrically biased at a RF voltage via the transmission of RF power from a RF generator 40 through an impedance match network 50 to substrate holder 20. The RF bias can serve to heat electrons to form and maintain plasma. In this configuration, the system can operate as a reactive ion etch (RIE) reactor, wherein the chamber and an upper gas injection electrode serve as ground surfaces. A typical frequency for the RF bias can range from 0.1 MHz to 100 MHz. RF systems for plasma processing are well known to those skilled in the art.

Alternately, RF power is applied to the substrate holder electrode at multiple frequencies. Furthermore, impedance match network 50 serves to improve the transfer of RF power to plasma in plasma processing chamber 10 by reducing the reflected power. Match network topologies (e.g. L-type, π-type, T-type, etc.) and automatic control methods are well known to those skilled in the art.

Vacuum pump system 30 can, for example, include a turbo-molecular vacuum pump (TMP) capable of a pumping speed up to 5000 liters per second (and greater) and a gate valve for throttling the chamber pressure. In conventional plasma processing devices utilized for dry plasma etch, a 1000 to 3000 liter per second TMP is generally employed. TMPs are useful for low pressure processing, typically less than 50 mTorr. For high pressure processing (i.e., greater than 100 mTorr), a mechanical booster pump and dry roughing pump can be used. Furthermore, a device for monitoring chamber pressure (not shown) can be coupled to the plasma processing chamber 10. The pressure measuring device can be, for example, a Type 628B Baratron absolute capacitance manometer commercially available from MKS Instruments, Inc. (Andover, Mass.).

Controller 14 comprises a microprocessor, memory, and a digital I/O port capable of generating control voltages sufficient to communicate and activate inputs to plasma processing system 1a as well as monitor outputs from plasma processing system 1a. Moreover, controller 14 can be coupled to and can exchange information with RF generator 40, impedance match network 50, the gas injection system (not shown), vacuum pump system 30, as well as the backside gas delivery system (not shown), the substrate/substrate holder temperature measurement system (not shown), and/or the electrostatic clamping system (not shown). For example, a program stored in the memory can be utilized to activate the inputs to the aforementioned components of plasma processing system 1a according to a process recipe in order to perform the method of removing photoresist from a substrate. One example of controller 14 is a DELL PRECISION WORKSTATION 610™, available from Dell Corporation, Austin, Tex.

Controller 14 can be locally located relative to the plasma processing system 1a, or it can be remotely located relative to the plasma processing system 1a. For example, controller 14 can exchange data with plasma processing system 1a using at least one of a direct connection, an intranet, and the internet. Controller 14 can be coupled to an intranet at, for example, a customer site (i.e., a device maker, etc.), or it can be coupled to an intranet at, for example, a vendor site (i.e., an equipment manufacturer). Additionally, for example, controller 14 can be coupled to the internet. Furthermore, another computer (i.e., controller, server, etc.) can, for example, access controller 14 to exchange data via at least one of a direct connection, an intranet, and the internet.

The diagnostic system 12 can include an optical diagnostic subsystem (not shown). The optical diagnostic subsystem can comprise a detector such as a (silicon) photodiode or a photomultiplier tube (PMT) for measuring the light intensity emitted from the plasma. The diagnostic system 12 can further include an optical filter such as a narrow-band interference filter. In an alternate embodiment, the diagnostic system 12 can include at least one of a line CCD (charge coupled device), a CID (charge injection device) array, and a light dispersing device such as a grating or a prism. Additionally, diagnostic system 12 can include a monochromator (e.g., grating/detector system) for measuring light at a given wavelength, or a spectrometer (e.g., with a rotating grating) for measuring the light spectrum such as, for example, the device described in U.S. Pat. No. 5,888,337.

The diagnostic system 12 can include a high resolution Optical Emission Spectroscopy (OES) sensor such as from Peak Sensor Systems, or Verity Instruments, Inc. Such an OES sensor has a broad spectrum that spans the ultraviolet (UV), visible (VIS), and near infrared (NIR) light spectrums. The resolution is approximately 1.4 Angstroms, that is, the sensor is capable of collecting 5550 wavelengths from 240 to 1000 nm. For example, the OES sensor can be equipped with high sensitivity miniature fiber optic UV-VIS-NIR spectrometers which are, in turn, integrated with 2048 pixel linear CCD arrays.

The spectrometers receive light transmitted through single and bundled optical fibers, where the light output from the optical fibers is dispersed across the line CCD array using a fixed grating. Similar to the configuration described above, light emitting through an optical vacuum window is focused onto the input end of the optical fibers via a convex spherical lens. Three spectrometers, each specifically tuned for a given spectral range (UV, VIS and NIR), form a sensor for a process chamber. Each spectrometer includes an independent A/D converter. And lastly, depending upon the sensor utilization, a full emission spectrum can be recorded every 0.1 to 1.0 seconds.

Figure 3:
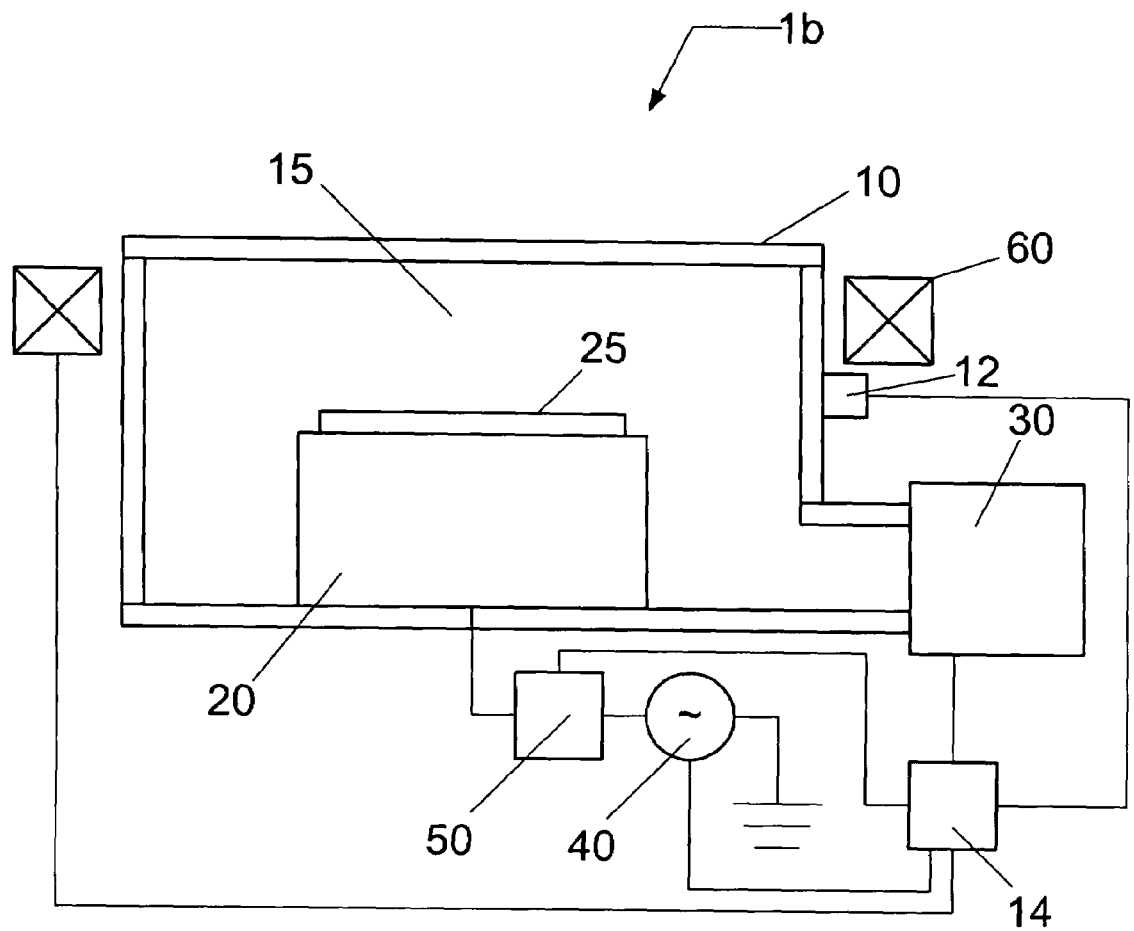
FIG. 3 shows a schematic diagram of a plasma processing system according to another embodiment of the invention.

In the embodiment shown in FIG. 3, the plasma processing system 1b can, for example, be similar to the embodiment of FIG. 1 or 2 and further comprise either a stationary, or mechanically or electrically rotating magnetic field system 60, in order to potentially increase plasma density and/or improve plasma processing uniformity, in addition to those components described with reference to FIG. 1 and FIG. 2. Moreover, controller 14 can be coupled to magnetic field system 60 in order to regulate the speed of rotation and field strength. The design and implementation of a rotating magnetic field is well known to those skilled in the art.

Figure 4:
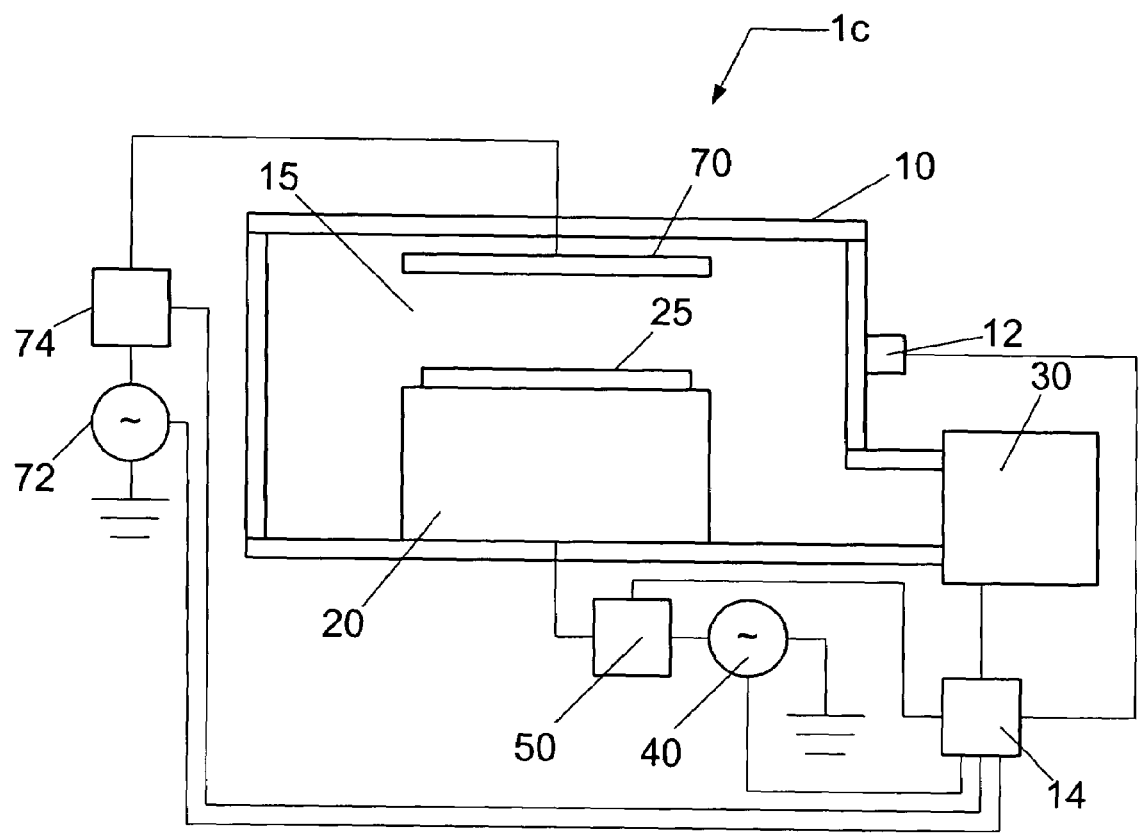
FIG. 4 shows a schematic diagram of a plasma processing system according to another embodiment of the invention.

In the embodiment shown in FIG. 4, the plasma processing system 1c can, for example, be similar to the embodiment of FIG. 1 or FIG. 2, and can further comprise an upper electrode 70 to which RF power can be coupled from RF generator 72 through impedance match network 74. A typical frequency for the application of RF power to the upper electrode can range from 0.1 MHz to 200 MHz. Additionally, a typical frequency for the application of power to the lower electrode can range from 0.1 MHz to 100 MHz. Moreover, controller 14 is coupled to RF generator 72 and impedance match network 74 in order to control the application of RF power to upper electrode 70. The design and implementation of an upper electrode is well known to those skilled in the art.

Figure 5:
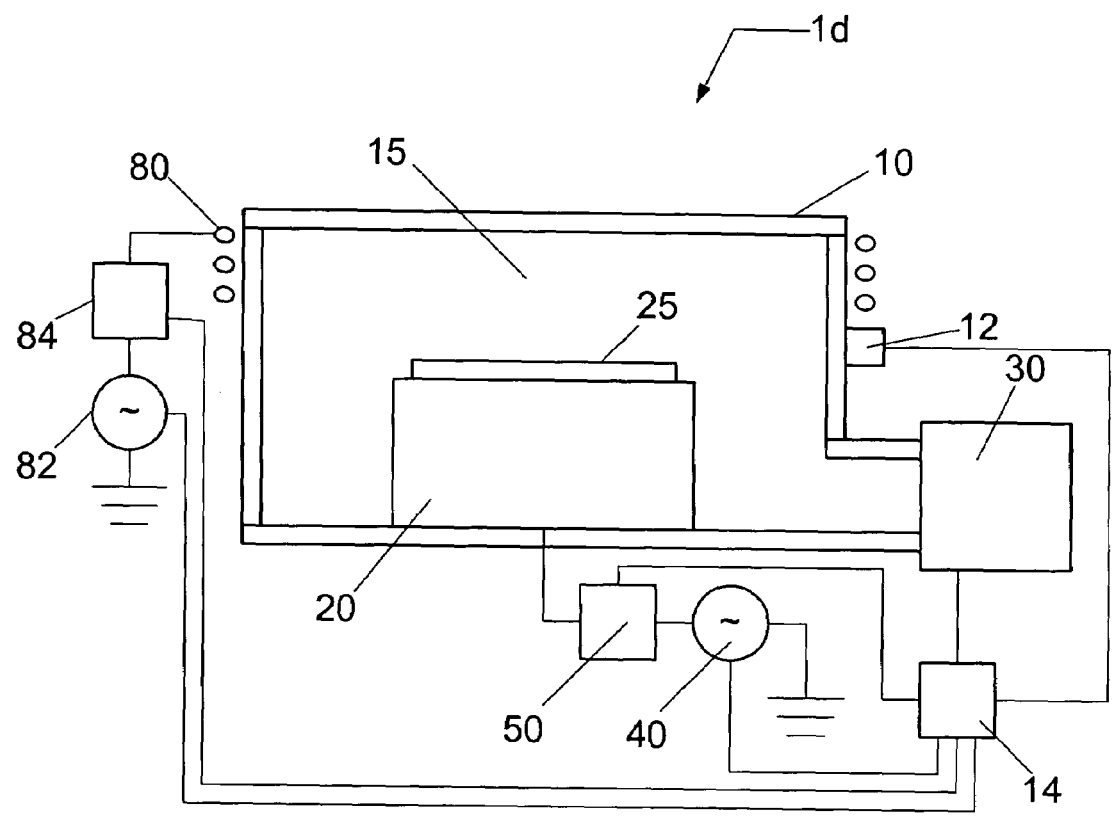
FIG. 5 shows a schematic diagram of a plasma processing system according to another embodiment of the invention.

In the embodiment shown in FIG. 5, the plasma processing system 1d can, for example, be similar to the embodiments of FIGS. 1 and 2, and can further comprise an inductive coil 80 to which RF power is coupled via RF generator 82 through impedance match network 84. RF power is inductively coupled from inductive coil 80 through dielectric window (not shown) to plasma processing region 45. A typical frequency for the application of RF power to the inductive coil 80 can range from 10 MHz to 100 MHz. Similarly, a typical frequency for the application of power to the chuck electrode can range from 0.1 MHz to 100 MHz. In addition, a slotted Faraday shield (not shown) can be employed to reduce capacitive coupling between the inductive coil 80 and plasma. Moreover, controller 14 is coupled to RF generator 82 and impedance match network 84 in order to control the application of power to inductive coil 80. In an alternate embodiment, inductive coil 80 can be a "spiral" coil or "pancake" coil in communication with the plasma processing region 15 from above as in a transformer coupled plasma (TCP) reactor. The design and implementation of an inductively coupled plasma (ICP) source, or transformer coupled plasma (TCP) source, is well known to those skilled in the art.

Alternately, the plasma can be formed using electron cyclotron resonance (ECR). In yet another embodiment, the plasma is formed from the launching of a Helicon wave. In yet another embodiment, the plasma is formed from a propagating surface wave. Each plasma source described above is well known to those skilled in the art.

In one embodiment, one or more seasoning substrates are processed in a plasma processing system, such as one of those described in FIGS. 1 through 5, in order to, for example, season an etch system for enhancing polymerization during subsequent plasma etch processes. The one or more seasoning substrates can, for instance, include silicon substrates blanket coated with a seasoning material, such as photo-resist. The present inventors have discovered that when optical emission spectroscopy is used to analyze a seasoning process, a light intensity spectrum of a coated substrate is different than the spectrum of a bare substrate. The present inventors have further discovered that using this difference, a bare wafer improperly introduced into a seasoning process can be identified so that corrective action may be taken.

Figure 6:
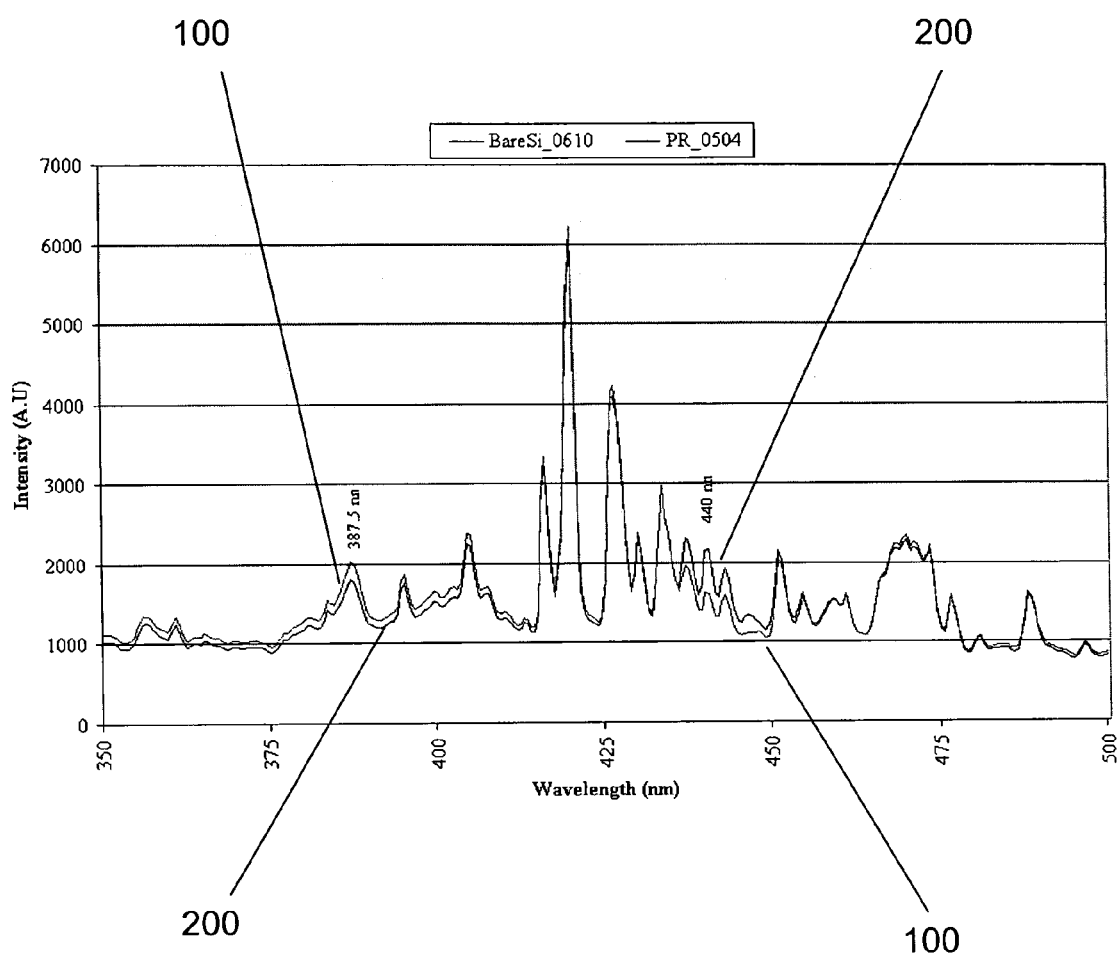
FIG. 6 presents exemplary optical emission spectra for a process in a plasma process system.

Referring now to FIG. 6, exemplary optical emission spectra are presented for a seasoning process. A first emission spectrum 100 is shown corresponding to a substrate blanket coated with photo-resist. A second emission spectrum 200 is also shown corresponding to a bare silicon substrate. The emission spectra can be obtained using optical emission spectroscopy, such as that described above. The seasoning process performed in FIG. 6 included exposing the substrate to a gaseous chemistry of $C_5F_8/O_2/Ar$, which is customarily used as a silicon oxide etch chemistry, for approximately 120 seconds. The data of FIG. 6 is intended to provide an example and not limit the scope of the invention in any way.

As shown in FIG. 6, the two spectra indicate spectral regions where there exists a noticeable difference in the light intensity. For instance, peaks at 387.5 nm and 440 nm demonstrate noticeable differences. In fact, the first emission spectrum 100 exhibits a higher light intensity at 387.5 nm, whereas the second emission spectrum 200 exhibits a higher light intensity at 440 nm. By taking a ratio of the light intensity at two spectral regions of the same spectra, such as 387.5 nm and 440 nm, the data, or ratio, is normalized, therefore, permitting its use from process-to-process despite different absolute values of intensity that may occur in different processes. Also, by taking a ratio, it permits selecting spectral regions that can provide a greater signal-to-noise ratio. For example, a first spectral region can be identified wherein the trend includes an increase in the light intensity for a bare silicon substrate relative to a photo-resist coated substrate, and a second spectral region can be identified wherein the trend includes a decrease in the light intensity for a bare silicon substrate relative to a photo-resist coated substrate. Such a selection of a first and second spectral region permits maximizing, or optimizing, the difference between the bare silicon substrate intensity ratio and the photo-resist coated substrate intensity ratio.

Figure 7:
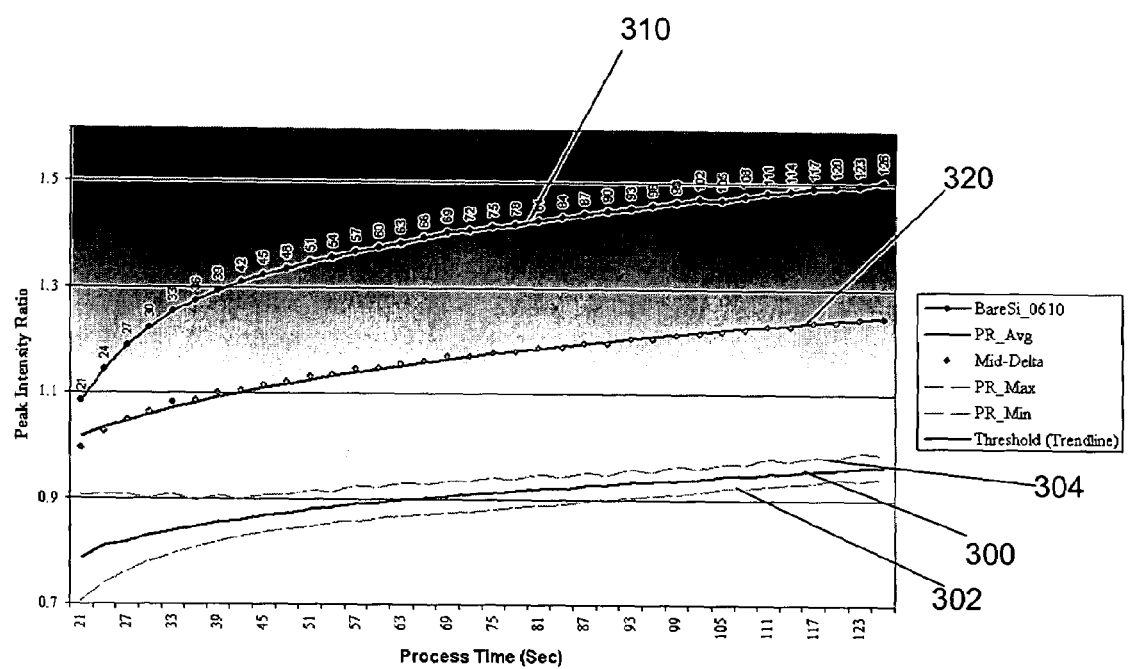
FIG. 7 presents exemplary optical signals for a process in a plasma processing system.

Referring now to FIG. 7, a first intensity ratio 300 is presented as a function of processing time. For example, the processing time is a measure of the amount of time a processing system is subjected to a seasoning process. The first intensity ratio 300 represents the light intensity ratio obtained when using seasoning substrates, such as blanket coated photo-resist substrates, during the seasoning process. The first intensity ratio 300 can represent a single seasoning substrate used during a seasoning process, or it may represent an average of a plurality of seasoning substrates executed with the seasoning process. In this example, the first intensity ratio represents an average of a plurality of seasoning substrate runs. As depicted in FIG. 7, a data minimum 302 represents the lower bound of the intensity ratio for the plurality of seasoning substrates, and a data maximum 304 represents the upper bound of the intensity ratio for the plurality of seasoning substrates.

Referring still to FIG. 7, a second intensity ratio 310 is presented as a function of processing time. For example, the processing time is a measure of the amount of time a processing system is subjected to a seasoning process. The second intensity ratio 310 represents the light intensity ratio obtained when using non-seasoning substrates, such as bare silicon substrates, during the seasoning process. The second intensity ratio 310 can represent a single non-seasoning substrate used during a seasoning process, or it may represent an average of a plurality of non-seasoning substrates executed with the seasoning process. In this example, the second intensity ratio 310 represents a single non-seasoning substrate used during the seasoning process. Also shown in FIG. 7, a threshold value 320 for the intensity ratio is presented as a function of processing time. For example, the threshold value can be the mid-point, or average, of the data maximum 304 and the second intensity ratio 310. The threshold value can be dynamic, or vary with time. Alternatively, the threshold value can be static, or constant. For example, the threshold value can be defined as the average of the threshold value 320 depicted in FIG. 7, i.e., approximately a value of 1.2.

Figure 8:
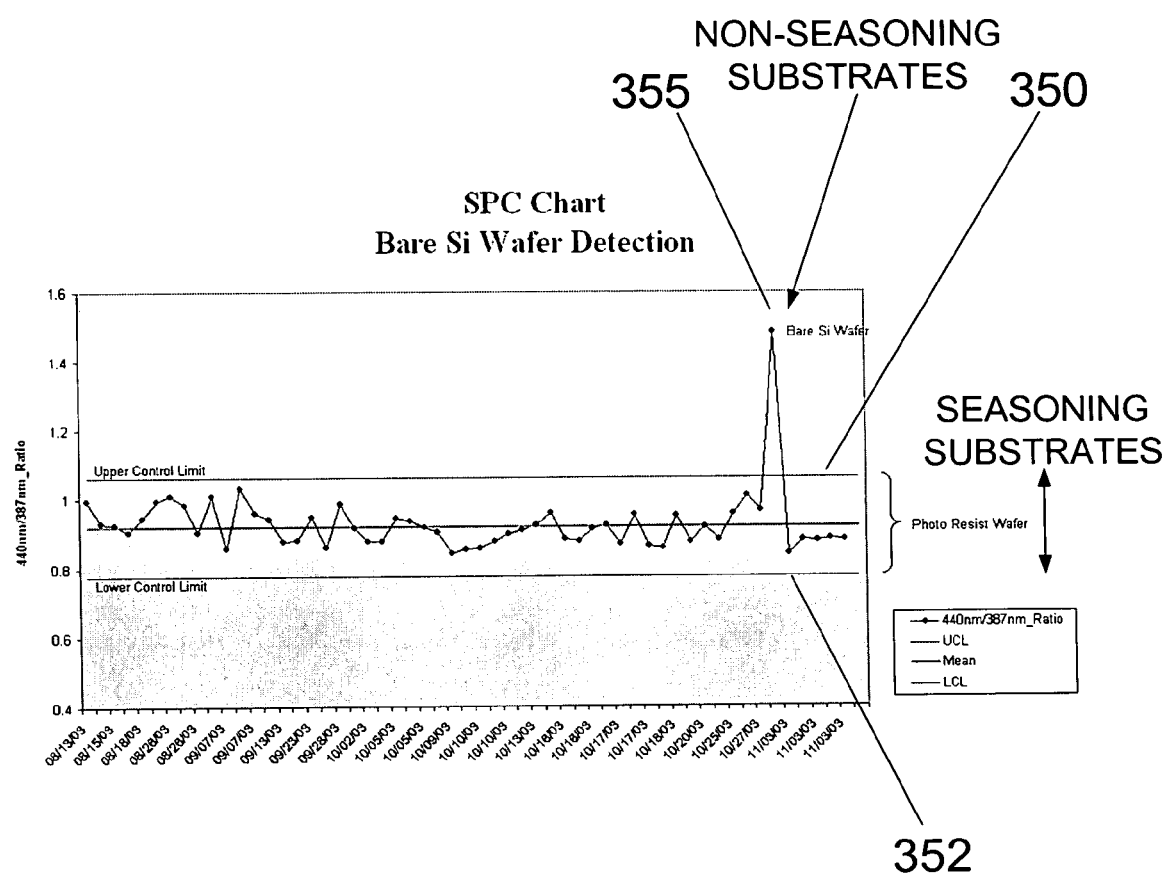
FIG. 8 presents additional exemplary optical signals for a process in a plasma processing system.

As noted above, the intensity spectra differences between coated and bare silicon substrates can be used to identify when an improper substrate type is introduced to a seasoning process. For example, FIG. 8 shows a statistical process control chart for monitoring a process for seasoning a chamber using a plurality of seasoning substrates, such as blanket coated photo-resist substrates. As seen in this figure, the acceptable intensity ratio for a proper seasoning substrate ranges from approximately 0.8 to slightly greater than 1.0. An upper static threshold value 350 of approximately 1.06 has been defined, and a lower static threshold value 352 of approximately 0.78 has been defined. When a non-seasoning substrate 355 is inserted into the seasoning process, the intensity ratio exceeds this upper static threshold value 350, and a fault can be deemed to have occurred and corrective action can be taken.

Figure 9:
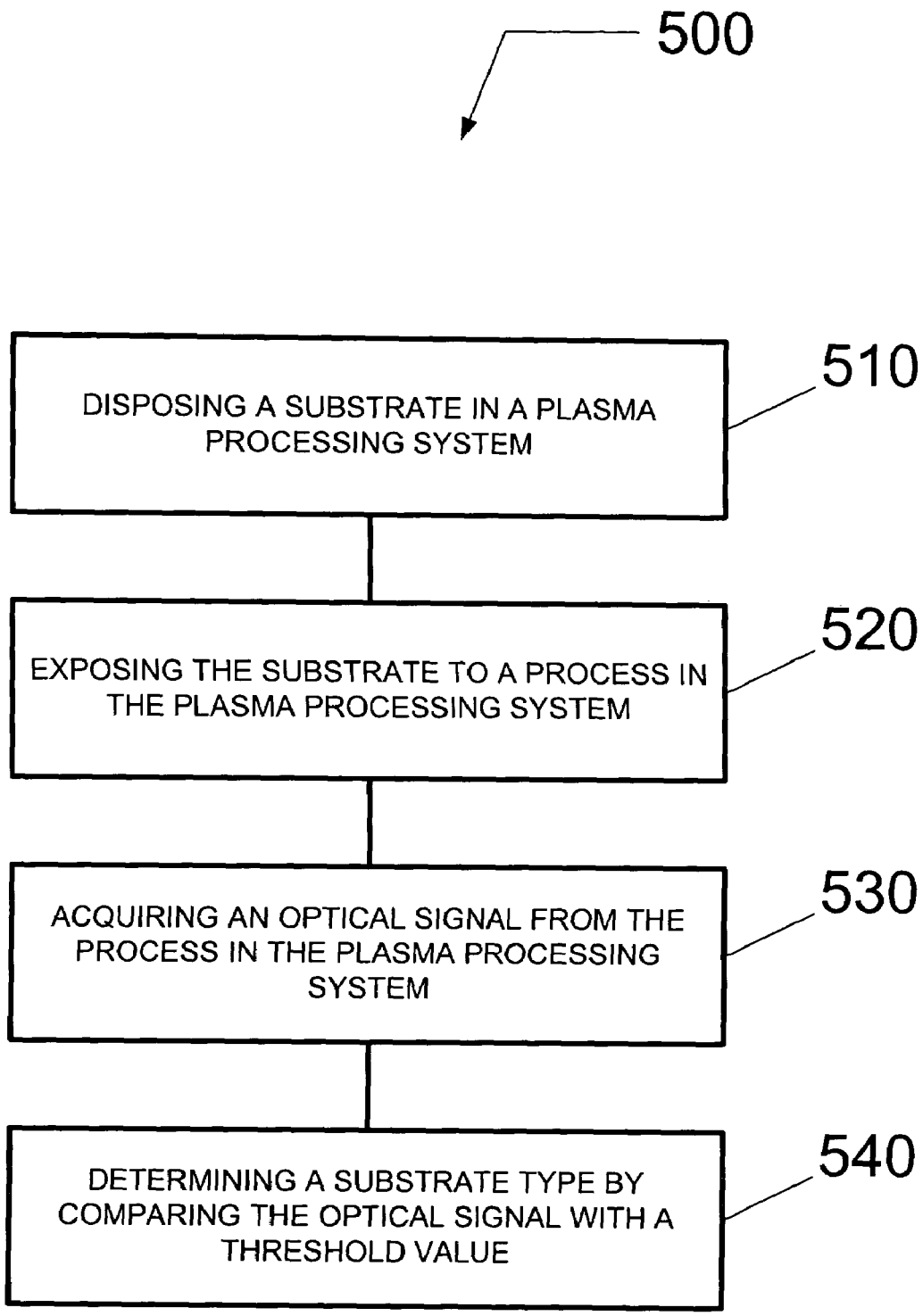
FIG. 9 presents a method of determining a substrate type according to an embodiment of the invention.

FIG. 9 presents a flow chart of a method for determining a substrate type according to an embodiment of the invention. The method includes a flow chart 500 beginning in 510 with disposing a substrate in a plasma processing system, such as any of the systems described in FIGS. 1–5 above.

In 520, the substrate is exposed to a seasoning process in the plasma processing system. The seasoning process can be specific to the process performed in the plasma processing system.

In 530, an optical signal is acquired from the plasma processing system. The optical signal can be acquired using a diagnostic system, such as an optical emission spectroscopy (OES) system. The optical signal can, for example, include a light intensity from a spectral range of an emission spectrum. Alternatively, the optical signal can, for example, include a ratio of light intensity from two or more spectral regions in an emission spectrum.

In 540, a substrate type is determined by comparing the optical signal with a threshold value. The substrate type can include either a correct substrate type, or an incorrect substrate type. For example, the correct substrate type can include a seasoning substrate, such as a blanket coated photo-resist substrate, and the incorrect substrate type can include a non-seasoning substrate, such as a bare silicon substrate. The threshold value can include a static, or constant, value. Alternatively, the threshold value can include a dynamic, or time varying, value. For instance, when the optical signal exceeds the threshold value, an operator can be alerted to the presence of a substrate of incorrect substrate type in the plasma processing system during a seasoning process. Corrective action can then be taken.

Corrective action typically includes removing the improper substrate from the process chamber, and ensuring that no further improper substrates will be inserted in the process chamber. Further corrective action depends largely on the seasoning process, the degree of the fault and the subsequent processing to be performed in the seasoned chamber. For example, some processes may tolerate a seasoned chamber where a single improper substrate was introduced during the seasoning process. In this case, corrective action may simply involve a notation that the seasoned chamber was exposed to an improper substrate during the seasoning process, so that process operators can consider this in making quality control assessments. Other processes may not tolerate even a single improper substrate during the seasoning process. In these cases, corrective action may involve cleaning of the process chamber and re-seasoning the chamber.

The identification of a substrate type as either a correct or incorrect substrate type, and the correction of the substrate type has been described in the context of a seasoning process for a processing system. However, substrate type identification can be utilized with production substrates as well. For example, when processing via substrates (i.e., substrates patterned for etching vias between metallization layers on the substrate) wherein the via pattern, for instance, comprises approximately 1% coverage on the substrate (i.e., photo-resist covers approximately 99% of the substrate), the via substrate can be distinguished from a bare silicon substrate using the methods described above. Additionally, for example, when processing trench substrates (i.e., substrates patterned for etching trenches for metallization layers on the substrate) wherein the trench pattern, for instance, comprises approximately 40 to 50% coverage on the substrate (i.e., photo-resist covers approximately 50 to 60% of the substrate), the trench substrate can be distinguished from a bare silicon substrate using the methods described above. Alternatively, via substrates can be distinguished from trench substrates. Therefore, during processing of production substrates, substrate type can be determined, and, when incorrect substrate types exist, corrective action can be taken. Depending upon the process (i.e., chemistry, etc.) and the type of substrates to be identified (i.e., via substrate versus bare silicon substrate), a threshold value can be determined using a method such as that described in FIGS. 7 and 8.

Although only certain embodiments of this invention have been described in detail above, those skilled in the art will readily appreciate that many modifications are possible in the embodiments without materially departing from the novel teachings and advantages of this invention. Accordingly, all such modifications are intended to be included within the scope of this invention.

What is claimed is:

1. A method for determining a substrate type comprising:
    disposing said substrate in a plasma processing system;
    exposing said substrate to a plasma process in said plasma processing system;
    detecting an optical signal resulting from an optical emission spectrum of said plasma process performed on said substrate, said optical signal including an intensity ratio of a first intensity corresponding to a first wavelength band to a second intensity corresponding to a second wavelength band; and
    determining whether said substrate type is a correct substrate type or an incorrect substrate type by comparing said optical signal with a threshold value,
    said threshold value comprises setting said threshold value to an average of an intensity ratio corresponding to the incorrect substrate type and an intensity ratio corresponding to the correct substrate type.

2. The method of claim 1, wherein said exposing said substrate to said process comprises exposing said substrate to a seasoning process.

3. The method of claim 1, wherein said detecting said optical signal comprises using optical emission spectroscopy (OES).

4. The method of claim 1, wherein said determining said substrate type comprises determining the correct substrate type when said intensity ratio has a value less than said threshold value, and determining the incorrect substrate type when said intensity ratio has a value greater than said threshold value.

5. The method of claim 1, wherein said determining said substrate type comprises identifying a seasoning substrate when said intensity ratio has a value less than said threshold value, and identifying a bare silicon substrate when said intensity ratio has a value greater than said threshold value.

6. The method of claim 1, wherein said comparing said optical signal with said threshold value comprises comparing said optical signal with at least one of a static threshold value, or a dynamic threshold value.

7. A method for determining a substrate type comprising:
disposing said substrate in a plasma processing system;
exposing said substrate to a seasoning process in said plasma processing system;
detecting an optical signal resulting from an optical emission spectrum of said process using optical emission spectroscopy, wherein said optical signal comprises an intensity ratio of a first intensity corresponding to a first wavelength band to a second intensity corresponding to a second wavelength band; and
determining whether said substrate is a correct substrate type or an incorrect substrate type by comparing said optical signal with a threshold value, wherein said threshold value is set to an average value between an intensity ratio for the correct substrate type and an intensity ratio for the incorrect substrate type.

8. The method of claim 1, wherein said exposing said substrate to said process comprises exposing said substrate to a production process.

* * * * *